United States Patent
Kim et al.

(10) Patent No.: US 10,220,106 B2
(45) Date of Patent: Mar. 5, 2019

(54) MOBILE PHONE CHARGER WITH STERILIZATION ULTRAVIOLET LED

(71) Applicant: Seoul Viosys Co., Ltd., Ansan-si (KR)

(72) Inventors: Jong Rack Kim, Ansan-si (KR); Dae Wong Suh, Ansan-si (KR); Seong Min Lee, Ansan-si (KR); Ik Hwan Ko, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 263 days.

(21) Appl. No.: 14/776,696

(22) PCT Filed: Feb. 26, 2014

(86) PCT No.: PCT/KR2014/001572
§ 371 (c)(1),
(2) Date: Sep. 14, 2015

(87) PCT Pub. No.: WO2014/142452
PCT Pub. Date: Sep. 18, 2014

(65) Prior Publication Data
US 2016/0030612 A1    Feb. 4, 2016

(30) Foreign Application Priority Data

Mar. 14, 2013  (KR) .................. 10-2013-0027465
Sep. 5, 2013   (KR) .................. 10-2013-0106885

(51) Int. Cl.
*H02J 7/00*    (2006.01)
*A61L 2/10*    (2006.01)

(52) U.S. Cl.
CPC .............. *A61L 2/10* (2013.01); *H02J 7/0027* (2013.01); *H02J 7/0044* (2013.01);
(Continued)

(58) Field of Classification Search
USPC ................................... 320/106–115
See application file for complete search history.

(56) References Cited

U.S. PATENT DOCUMENTS

2002/0132651 A1    9/2002   Jinnouchi
2004/0147293 A1*   7/2004   Park ................. H04M 1/04
                                                    455/573
(Continued)

FOREIGN PATENT DOCUMENTS

CN    201122642 Y    9/2008
CN    202605362 U    12/2012
(Continued)

OTHER PUBLICATIONS

Park, H. L., Authorized Officer, Korean Intellectual Property Office, International Search Report, International Application No. PCT/KR2014/001572, dated Jun. 5, 2014, 2 pages.
(Continued)

*Primary Examiner* — Binh Tat
(74) *Attorney, Agent, or Firm* — Perkins Coie LLP (57) ABSTRACT

A mobile phone charger with a sterilization UV LED may include: a charger case having a space formed therein and including a mobile phone stand formed at the front surface thereof; and one or more first UV LEDs installed at one side of the space of the charger case.

16 Claims, 5 Drawing Sheets

(52) U.S. Cl.
CPC .......... *H02J 7/0045* (2013.01); *H02J 7/0052* (2013.01); *A61L 2202/16* (2013.01)

(56) References Cited

U.S. PATENT DOCUMENTS

| | | | | |
|---|---|---|---|---|
| 2014/0265998 A1* | 9/2014 | Nielson | ................ | H02J 7/0047 320/101 |
| 2015/0137762 A1* | 5/2015 | Kim | ...................... | H02J 7/0044 320/115 |

FOREIGN PATENT DOCUMENTS

| | | | |
|---|---|---|---|
| JP | 2004-112980 A | 4/2004 | |
| KR | 20-0297001 Y1 | 11/2002 | |
| KR | 10-2011-0083073 A | 7/2011 | |

OTHER PUBLICATIONS

Second Office Action in Chinese Patent Application No. 201480015293.9, dated Feb. 24, 2018.

Chinese Office Action from corresponding Chinese Patent Application No. 201480015293.9, dated Nov. 21, 2018.

\* cited by examiner

MOBILE PHONE CHARGER WITH
STERILIZATION ULTRAVIOLET LED

CROSS REFERENCE TO RELATED
APPLICATION

This patent document is a 35 U.S.C. § 371 National Stage application of PCT Application No. PCT/KR2014/001572, filed on Feb. 26, 2014, which further claims the benefits and priorities of prior Korean Patent Application No. 10-2013-0027465, filed on Mar. 14, 2013, and prior Korean Patent Application No. 10-2013-0106885, filed on Sep. 5, 2013. The entire disclosures of the above applications are incorporated by reference in their entirety as part of this document.

TECHNICAL FIELD

The present invention relates to a mobile phone charger, and more particularly, to a mobile phone charger with a sterilization ultraviolet (UV) LED.

BACKGROUND ART

Recently, a portable terminal such as a mobile phone has been common to such an extent that almost everyone ranging from adults to teenagers carries a portable terminal. Furthermore, the portable terminal is becoming a necessity of modern life. Although such a portable terminal offers great convenience to modern life, various bacteria existing on the portable terminal may have a bad effect on a user's body because the portable terminal is carried at all times. In particular, most of portable terminals which are recently used include a touch screen operated through a touch of a user's finger. Thus, when a screen area of a portable terminal is insanitary, a user becomes highly likely to be infected with harmful bacteria. Recently, a sterilization device has been proposed, which is capable of sterilizing a mobile phone during a charging operation.

The conventional sterilization device includes a sterilization unit using a UV lamp, and is configured to charge only a battery of the mobile phone or charge the mobile phone using an adapter. In the conventional sterilization device, however, the UV lamp occupies a large space to thereby make it difficult to design a product. Thus, the conventional sterilization device has a limit to miniaturization and ultra-miniaturization. Furthermore, the conventional sterilization device cannot perform sterilization at the same time while the portable terminal is charged. When the UV lamp is broken by an external impact, mercury or the like leaking from the UV lamp may cause environmental pollution, and have a fatal influence on user's health. Furthermore, due to the characteristic of the UV lamp, the UV lamp cannot intensively sterilize a specific portion of the portable terminal. Thus, the sterilization efficiency inevitably decreases.

DISCLOSURE OF INVENTION

Technical Problem

Embodiments of the present invention are directed to a mobile phone charger with a sterilization UV LED, which is capable of performing a sterilization operation while charging a mobile phone.

Solution to Problem

In one embodiment, a mobile phone charger with a sterilization UV LED may include: a charger case having a space formed therein and including a mobile phone stand formed at the front surface thereof; and one or more first UV LEDs installed at one side of the space of the charger case.

The mobile phone stand may include: a mounting groove formed at the front surface of the charger case so as to communicate with the space; an edge surface formed along the edge of the mounting groove so as to support the edge of the mobile phone; and a bump protruding from the bottom of the charger case so as to support the bottom of the mobile phone.

At this time, the first UV LEDs may be mounted in the mounting groove.

In another embodiment, a mobile phone charger with a sterilization UV LED may include: a charger case having a first insertion groove for inserting a mobile phone and a second insertion groove for inserting a battery wherein the first insertion groove and the second insertion groove are formed separately from each other; and one or more second UV LEDs provided in the charger case so as to sterilize the mobile phone and the battery.

The mobile phone charger may further include a speaker case installed at one side of the charger case and having a speaker installed therein.

The mobile phone charger may further include: a speaker grill provided on the surface of the speaker case so as to protect the speaker; and one or more third UV LEDs installed in the speaker case.

The speaker grill may be coated with photocatalyst for air cleaning.

The photocatalyst for air cleaning may include $TiO_2$.

The mobile phone charger may further include an operation sensor provided at one side of the charger case so as to stop the operation of the first UV LEDs or the second UV LEDs.

In another embodiment, a mobile phone charger with a sterilization UV LED may include: a charger body performing a charging operation on a mobile phone mounted on one surface; a handle folded from one side of the charger body to the top of the charger body; and a sterilization UV LED attached to the inner surface of the handle.

The sterilization UV LED may include a plurality of UV LEDs.

Power may be supplied to the sterilization UV LED as soon as the handle is lifted.

The mobile phone charger may further include a switch to manually supply power to the sterilization UV LED.

The mobile phone charger may further include a reflecting plate interlocked with the handle, disposed at one side of the mobile phone when the handle is lifted, and reflecting UV light emitted from the sterilization UV LED toward the mobile phone, thereby increasing sterilization efficiency.

Advantageous Effects of Invention

In accordance with the embodiment of the present invention, the mobile phone charger with a sterilization UV LED may sterilize a mobile phone through UV LEDs while charging the mobile phone, thereby protecting a user's health. At this time, only the sterilization operation may be performed without charging the mobile phone. Furthermore, the mobile phone charger may prevent the environmental pollution caused by the conventional sterilization UV lamp, thereby protecting a user's health. Furthermore, the mobile phone charger may intensively sterilize a portion which needs to be sterilized may be intensively sterilized, using the UV LEDs, and the compact configuration of the mobile phone charger may improve the degree of freedom of design for a product.

BRIEF DESCRIPTION OF DRAWINGS

The accompanying drawings, together with the specification, illustrate some exemplary embodiments of the present invention, and, together with the description, serve to explain principles and aspects of the present invention.

BEST MODE FOR CARRYING OUT THE INVENTION

Embodiments of the invention will hereinafter be described in detail with reference to the accompanying drawings. It should be noted that the drawings are not to precise scale and may be exaggerated in thickness of lines or sizes of components for descriptive convenience and clarity only. Furthermore, the terms as used herein are defined by taking functions of the invention into account and can be changed according to the custom or intention of users or operators. Therefore, definition of the terms should be made according to the overall disclosures set forth herein.

Figure 1:
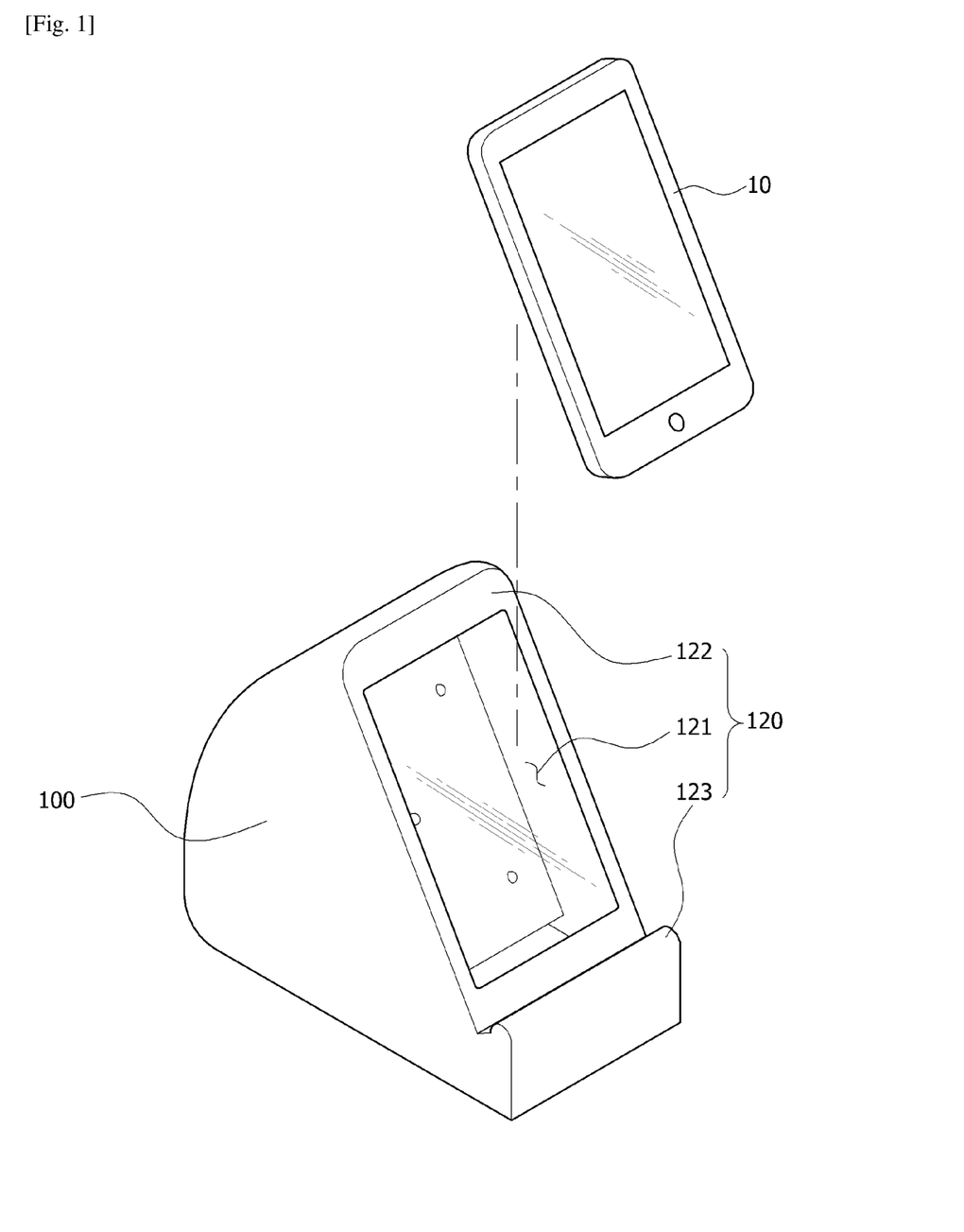
FIG. 1 is a perspective view of a mobile phone charger with a sterilization UV LED in accordance with an embodiment of the present invention.
Figure 2:
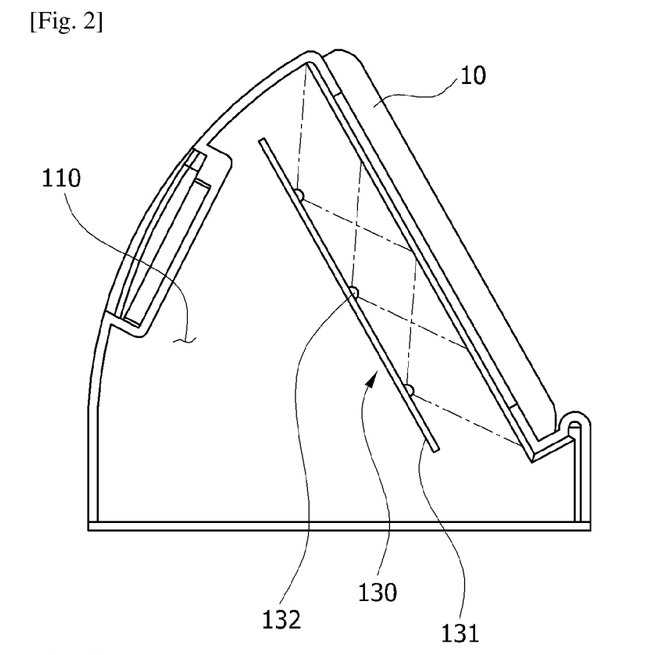
FIG. 2 is a cross-sectional view of the mobile phone charger with a sterilization UV LED in accordance with the embodiment of the present invention.

FIG. 1 is a perspective view of a mobile phone charger with a sterilization UV LED in accordance with an embodiment of the present invention. FIG. 2 is a cross-sectional view of the mobile phone charger with a sterilization UV LED in accordance with the embodiment of the present invention. As illustrated in FIGS. 1 and 2, the mobile phone charger with a sterilization UV LED in accordance with the embodiment of the present invention (hereafter, referred to as the charger) may include a charger case 100 and a light emitting unit 130. The charger case 100 may have a space 110 formed therein and include a mobile phone stand 120 formed on the front surface thereof, and the light emitting unit 130 may be installed at one side of the space 110 of the charger case 110 and include one or more first UV LEDs. The mobile phone stand 120 may include a mounting groove 121, an edge surface 122, and a bump 123. The mounting groove 121 may be formed at the front surface of the charger case 100 so as to communicate with the space 110, the edge surface 122 may be formed along the edge of the mounting groove 121 so as to support the edge of the mobile phone 10, and the bump 123 may protrude from the bottom of the charger case 100 so as to support the bottom of the mobile phone 10. At this time, the mobile phone stand 20 may further include a transparent window provided at the front surface of the mounting groove 121. Furthermore, the front surface of the charger case 100 may be inclined in such a manner that the mobile phone 10 is placed to lean against the front surface, and the rear surface of the charger case 100 may be formed to be rounded. Furthermore, the light emitting unit 130 may include one or more first UV LEDs, and may be formed in such a manner that a plurality of UV LED chips 132 are mounted on a substrate 131. At this time, the first UV LED may include a top view or side view-type UV LED.

The light emitting unit 130 may be installed in the mounting groove 121 of the charger case 100, and the first UV LED may emit light at a wavelength of 200 to 400 nm for sterilization. Thus, the surface of the mobile phone 10 placed on the mobile phone stand 120 (for example, a display screen) may be sterilized through the first UV LEDs. If necessary, the first UV LEDs may be concentrated at an area of the mounting groove 121, which faces a specific portion of the mobile phone 10 when the mobile phone 10 is placed on the mobile phone stand 120, thereby intensively sterilizing the specific portion of the mobile phone 10. At this time, the mobile phone 10 placed on the mobile phone stand 120 may be selectively charged or sterilized, or may be charged and sterilized at the same time. The sterilization function may be performed only for a predetermined time. Furthermore, an operation sensor (not illustrated) may be provided at one side of the charger case 100. In this case, when the operation sensor senses an action around the charger, the operation of the light emitting unit 130 may be stopped to secure user's safety. At this time, when the first UV LEDs are exposed to the outside, the circuit may be forcibly shorted to completely stop the operation of the light emitting unit 130, or coupled to automatically operate the light emitting unit 130. Furthermore, in order to increase the sterilization effect, a reflecting cover (not illustrated) may be provided at one side of the light emitting unit 130 so as to cover the mobile phone 10. The reflecting cover may be formed of a material having high reflectivity.

Figure 3:
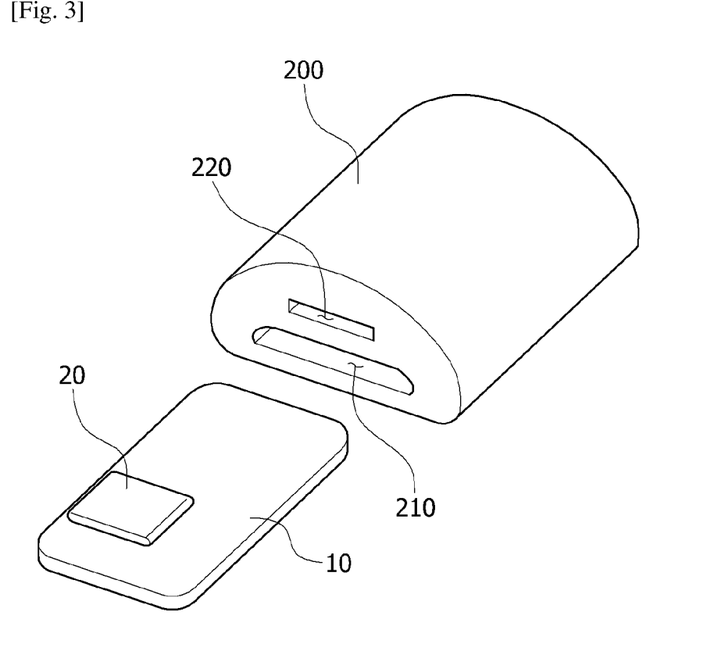
FIGS. 3 and 4 are perspective views of a mobile phone charger with a sterilization UV LED in accordance with another embodiment of the present invention.
Figure 4:
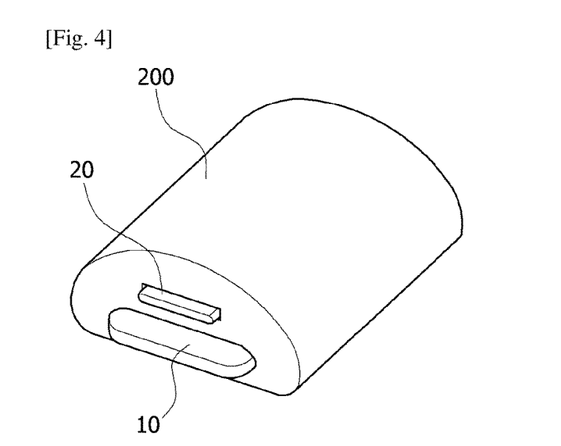

FIGS. 3 and 4 are perspective views of a mobile phone charger with a sterilization UV LED in accordance with another embodiment of the present invention. The charger in accordance with the present embodiment has substantially the same function as the embodiment described with reference to FIGS. 1 and 2, but is different from the embodiment described with reference to FIGS. 1 and 2 in that a mobile phone 10 and a battery 20 are slid and mounted in a charger case 200. Thus, the detailed descriptions of the same functions and components as the above-described embodiment are omitted herein.

The charger in accordance with the present embodiment may include the charger case 200 and a light emitting unit (not illustrated). The charger case 200 may have a first insertion groove 210 for inserting the mobile phone 10 and a second insertion groove 220 for inserting the battery 20. The first insertion groove 210 and the second insertion groove 220 may be formed separately from each other. The light emitting unit may include one or more second UV LEDs provided in the charger case 200 so as to sterilize the mobile phone 10 and the battery 20. At this time, the charger case 200 may have a flat bottom surface so as to be laid down, and the top surface of the charger case 200 may be convexly curved. Furthermore, the mobile phone 10 and the battery 20 may be sterilized and charged at the same time, or any one of the mobile phone 10 and the battery 20 may be selectively sterilized or charged. Like the above-described embodiment, the charger may further include a circuit or operation sensor for turning off the light emitting unit in a predetermined time or controlling the operation of the light emitting unit.

Figure 5:
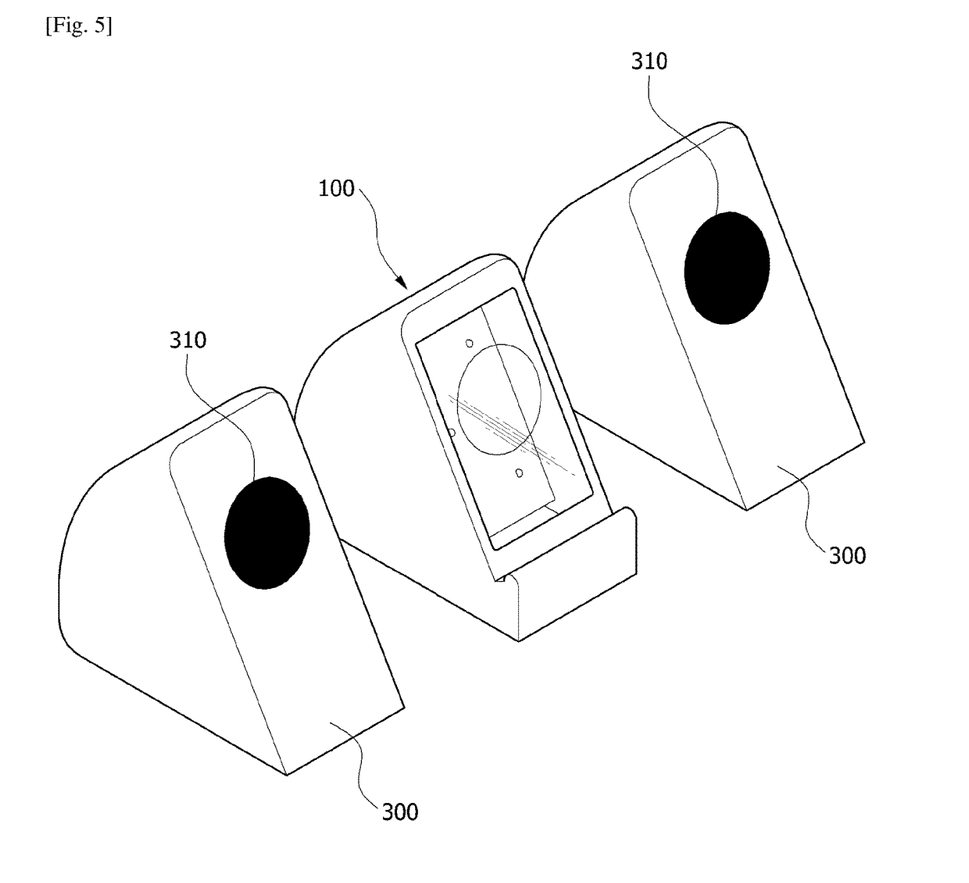
FIG. 5 is a diagram illustrating a state in which the mobile phone charger with a sterilization UV LED in accordance with the embodiment of the present invention is used.

FIG. 5 is a diagram illustrating a state in which the mobile phone charger with a sterilization UV LED in accordance with the embodiment of the present invention is used. As illustrated in FIG. 5, the charger in accordance with the embodiment of the present invention may further include a speaker. Such a configuration may be applied to the embodiment illustrated in FIGS. 3 and 4. At this time, a user may listen to the sound of music or video stored in the mobile phone 10 through the speaker, and the speaker may be installed in a pair of speaker cases 300 installed at one side or both sides of the charger case 100. The speaker cases 300 may have a similar shape to the charger case 100 illustrated in FIG. 2. That is, the speaker cases 300 may have an inclined surface formed at the front surface thereof and a rounded surface formed at the rear surface thereof. At this time, the speaker cases 300 may include a speaker grill 310 formed on the front surface thereof and a light emitting unit (not illustrated) installed therein. The speaker grill 310 may serve to prevent the permeation of foreign matters or moisture and protect a diaphragm of the speaker, and the light emitting unit may include one or more third UV LEDs. At this time, the light emitting unit may include a plurality of top view or side view-type UV LEDs mounted on a substrate, like the above-described embodiment. The surface of the speaker case 300, or desirably, the speaker grill 310 may be coated with photocatalyst for air cleaning. More desirably, the surface of the speaker case 300 may be coated with $TiO_2$ for an air cleaning function of removing environmental hormone using UV light emitted from the light emitting unit.

As such, when the speaker cases 300 having an air cleaning function are installed at both sides of the charger case 100 or 200 in accordance with the above-described embodiment, a user may listen to the sound of music or video while performing the charging and/or sterilization operation. At this time, the air cleaning operation may also be performed at the same time.

Figure 6:
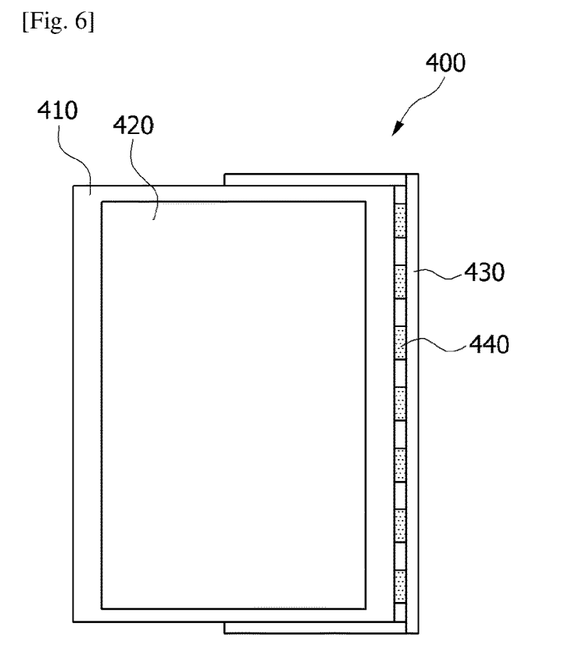
FIG. 6 is a plan view illustrating a state in which a handle of a mobile phone charger with a sterilization UV LED in accordance with another embodiment of the present invention is folded.
Figure 7:
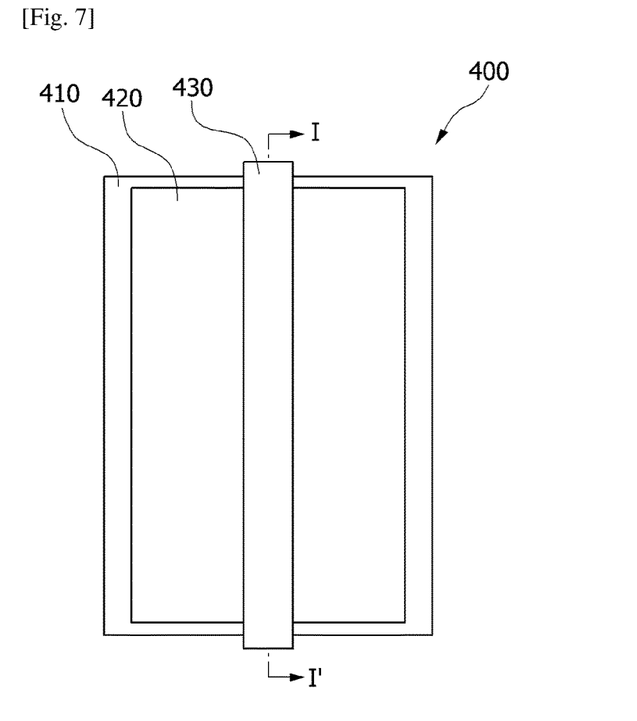
FIG. 7 is a plan view illustrating a state in which the handle of the mobile phone charger with a sterilization UV LED in accordance with the embodiment of the present invention is lifted.

FIG. 6 is a plan view illustrating a state in which a handle of a mobile phone charger with a sterilization UV LED in accordance with another embodiment of the present invention is folded. FIG. 7 is a plan view illustrating a state in which the handle of the mobile phone charger with a sterilization UV LED in accordance with the embodiment of the present invention is lifted. Referring to FIGS. 6 and 7, the charger 400 in accordance with the embodiment of the present invention may include a charger body 410 which charges a mobile phone 420 when the mobile phone 420 is mounted thereon. The power supply from the charger body 410 may be performed in a wired or wireless manner. The charger body 410 may include a foldable handle 430 attached thereon. As illustrated in FIG. 6, the handle 430 may be positioned at one side of the charger body 410 in a state where it is folded. Furthermore, as illustrated in FIG. 7, the handle 430 may be positioned at the center of the charger body 410 in a state where it is lifted. The handle 430 may include a plurality of sterilization UV LEDs 440 attached on an inner surface thereof. Thus, when the handle 430 is lifted to the center of the charger body 410, the plurality of sterilization UV LEDs 440 may be disposed to face the surface of the mobile phone 420. Then, UV light emitted from the sterilization UV LEDs 440 may be transmitted to the surface of the mobile phone 420. In an example, the sterilization UV LEDs 440 may be configured in a module type.

Although not illustrated, a charging circuit may be disposed in the charger body 410 so as to perform a charging operation on the mobile phone 420. The charging circuit may be connected to the sterilization UV LEDs 440 attached on the handle 430. The connection between the charging circuit and the sterilization UV LEDs 440 may be performed through a switch on/off operation which is automatically performed according to a predetermined condition. For example, as illustrated in FIG. 6, the charging circuit may be switched off in a state where the handle 430 is folded at the side of the charger body 410. In this case, no power is supplied to the sterilization UV LEDs 440 attached to the handle 430, and the sterilization UV LEDs 440 may maintain an off-state. On the other hand, as illustrated in FIG. 7, when the handle 430 is lifted over the charger body 410, the charging circuit may be switched on. In this case, power is supplied to the sterilization UV LEDs 440 attached to the handle 430, and the sterilization UV LEDs 440 may be switched on to perform a sterilization operation using UV light. The charging circuit connected to the sterilization UV LEDs 440 may be switched on as soon as the handle 430 starts to be lifted. In this case, even while the handle 430 is lifted, a sterilization operation may be performed. In another example, power may be manually supplied to the sterilization UV LEDs 440. In this case, the charger may further a separate switch to turn on/off the power supply to the sterilization UV LEDs 440.

Figure 8:
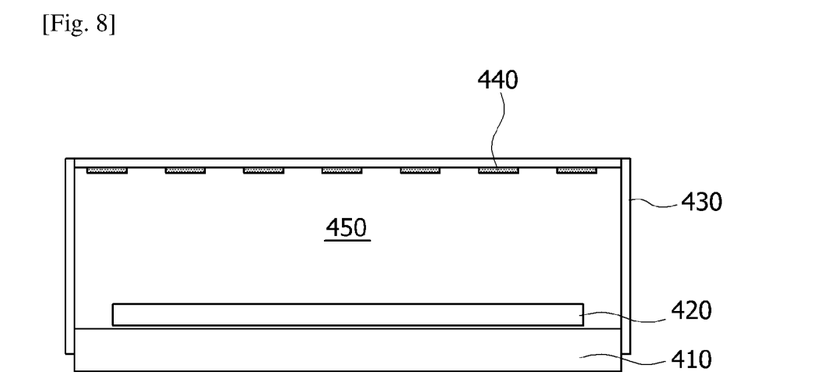
FIG. 8 is a cross-sectional view illustrating an example of a cross-sectional structure taken along line I-I' of FIG. 7.

FIG. 8 is a cross-sectional view illustrating an example of a cross-sectional structure taken along line I-I' of FIG. 7. Referring to FIGS. 7 and 8, a charging target, for example, the mobile phone 420 may be mounted on the charger body 410. In this state, when the handle 430 is lifted over the charger body 410, power may be automatically supplied to the sterilization UV LEDs 440 attached to the handle 430, and the sterilization UV LEDs 440 attached to the handle 430 lifted over the charger body 410 may emit UV light. The emitted UV light may be transmitted to the space 450 between the mobile phone 420 and the handle 430, and then sterilize the mobile phone 420.

Figure 9:
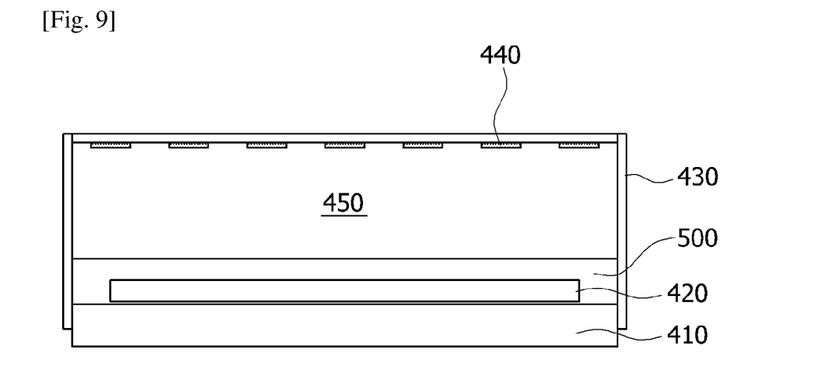
FIG. 9 is a cross-sectional view illustrating another example of the cross-sectional structure taken along line I-I' of FIG. 7.

FIG. 9 is a cross-sectional view illustrating another example of the cross-sectional structure taken along line I-I' of FIG. 7. Referring to FIGS. 9 and 7, a charging target, for example, the mobile phone 420 may be mounted on the charger body 410. In this example, the handle 430 may be attached to a reflecting plate 500. When the handle 430 is lifted over the charger body 410, the reflecting plate 500 may be moved with the handle 430 and disposed at a side of the mobile phone 420. As the handle 430 is lifted over the charger body 410, power may be automatically supplied to the sterilization UV LEDs 440 attached to the handle 430. As power is supplied to the sterilization UV LEDs 440, the sterilization UV LEDs 440 attached to the handle 430 lifted over the charger body 410 may emit UV light. The emitted UV light may be transmitted to the space 450 between the mobile phone 420 and the handle 430, and then sterilize the mobile phone 420. At this time, the reflecting plate 500 may reflect UV light transmitted toward the side of the mobile phone 420 such that the UV light faces the mobile phone 420, thereby improving the sterilization efficiency of the UV light.

Although some embodiments have been provided to illustrate the invention in conjunction with the drawings, it will be apparent to those skilled in the art that the embodiments are given by way of illustration only, and that various modifications and equivalent embodiments can be made without departing from the spirit and scope of the invention. The scope of the invention should be limited only by the accompanying claims.

The invention claimed is:

1. A mobile phone charger with a sterilization UV LED, comprising:
   a charger case including an internal space surrounded by an exterior surface including a front surface providing a space for receiving a mobile phone;
   a substrate positioned in the internal space to face the front surface and spaced away by a distance from the front surface; and
   a plurality of UV LEDs installed on the substrate to provide UV radiation toward the mobile phone; and
   a transparent window provided on the front surface to transmit UV light emitted by the plurality of UV LEDs, and
   wherein the UV LEDs in the plurality of UV LEDs are arranged to be separated from one another such that UV radiation beams emitted by at least two UV LEDs towards the mobile phone overlap with each other and the UV radiation beams from the plurality of UV LEDs cover a whole area of the front surface.

2. The mobile phone charger of claim 1, wherein the charger case further comprises:
   a mounting groove formed at the front surface of the charger case and configured to communicate with the internal space;
   an edge surface formed along the mounting groove and configured to support the mobile phone; and
   a bump protruding from a bottom of the charger case and configured to support the mobile phone.

3. The mobile phone charger of claim 1, wherein the UV LEDs are arranged to face the front surface.

4. The mobile phone charger of claim 1, further comprising a speaker case installed at one side of the charger case and having a speaker installed inside of the speaker case.

5. The mobile phone charger of claim 4, further comprising:
   a speaker grill provided on a surface of the speaker case; and
   one or more additional UV LEDs installed in the speaker case.

6. The mobile phone charger of claim 5, wherein the speaker grill is coated with photocatalyst for air cleaning.

7. The mobile phone charger of claim 6, wherein the photocatalyst for air cleaning comprises $TiO_2$.

8. The mobile phone charger of claim 1, further comprising an operation sensor provided in the charger case and configured to selectively stop the operation of the UV LEDs.

9. The mobile phone charge of claim 1, wherein the mobile phone includes a portable terminal.

10. The mobile phone charger of claim 1, wherein at least one of the plurality of UV LEDs includes a top view or side view typed UV LED.

11. The mobile phone charger of claim 1, wherein the UV radiation provided by the plurality of UV LEDs has a wavelength of 200 to 400 nm.

12. The mobile phone charger of claim 1, wherein the front surface of the charger case is inclined with respect to a bottom surface of the charger case.

13. The mobile phone charger of claim 1, further comprising a cover positioned at one side of the light emitting unit and including a reflecting material.

14. The mobile phone charger of claim 1, wherein the exterior surface has a curved portion.

15. The mobile phone charger of claim 1, wherein the substrate extends in a direction parallel to the front surface of the charger case.

16. The mobile phone charger of claim 1, wherein the front surface has a shape extending along the substrate is positioned parallel to the first surface.

* * * * *